(12) United States Patent
Kohler et al.

(10) Patent No.: US 9,188,545 B2
(45) Date of Patent: Nov. 17, 2015

(54) CONTAINER INSPECTION APPARATUS AND METHOD

(75) Inventors: Timothy A. Kohler, Waterville, OH (US); Stephen M. Graff, Maumee, OH (US); George H. Hall, Jr., Toledo, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 201 days.

(21) Appl. No.: 13/283,961

(22) Filed: Oct. 28, 2011

(65) Prior Publication Data

US 2013/0107249 A1    May 2, 2013

(51) Int. Cl.
*G01N 21/00* (2006.01)
*G01N 21/90* (2006.01)
*G01B 11/12* (2006.01)
*G01B 11/24* (2006.01)

(52) U.S. Cl.
CPC ............ *G01N 21/9054* (2013.01); *G01B 11/12* (2013.01); *G01B 11/24* (2013.01)

(58) Field of Classification Search
CPC ......... G01B 11/24; G01B 11/10; G01N 21/90
USPC .............. 356/239.4, 237.1; 250/223; 382/142
See application file for complete search history.

(56) References Cited

U.S. PATENT DOCUMENTS

| | | | | |
|---|---|---|---|---|
| 3,651,937 A | * | 3/1972 | Kronseder | 209/524 |
| 3,708,680 A | * | 1/1973 | Calhoun | 250/223 B |
| 3,923,158 A | * | 12/1975 | Fornaa | 209/526 |
| 4,026,414 A | * | 5/1977 | Ellinger | 209/524 |
| 4,256,957 A | * | 3/1981 | Ford et al. | 250/223 B |
| 4,448,526 A | * | 5/1984 | Miyazawa | 356/237.1 |
| 4,454,542 A | * | 6/1984 | Miyazawa | 348/127 |
| 4,682,023 A | * | 7/1987 | Yoshida | 250/223 B |
| 4,906,098 A | * | 3/1990 | Thomas et al. | 356/612 |
| 4,914,289 A | * | 4/1990 | Nguyen et al. | 250/223 B |
| 4,922,543 A | * | 5/1990 | Ahlbom et al. | 382/291 |
| 4,943,713 A | * | 7/1990 | Yoshida | 250/223 B |
| 4,959,537 A | * | 9/1990 | Kimoto et al. | 250/223 B |
| 5,216,239 A | * | 6/1993 | Yoshida | 250/223 B |
| 5,461,228 A | | 10/1995 | Kirkman et al. | |

(Continued)

FOREIGN PATENT DOCUMENTS

| | | |
|---|---|---|
| DE | 94 01 449.3 U1 | 3/1994 |
| EP | 0 676 634 A1 | 10/1995 |
| JP | 55071938 A | 5/1980 |

OTHER PUBLICATIONS

International Search Report and Written Opinion, International Application No. PCT/US2012/058245, International Filing Date: Oct. 1, 2012, Mailing Date: Feb. 6, 2013, 12 pages.

*Primary Examiner* — Tarifur Chowdhury
*Assistant Examiner* — Isiaka Akanbi (57) ABSTRACT

A method of and apparatus for inspecting a container having a base and a mouth. Light is directed through the container base into the container, and out of the container through the container mouth, using at least one light source disposed beneath the container base. A plurality of images of the container mouth is obtained from the light transmitted through the container mouth. Minimum bore diameters of the container mouth are calculated from the plurality of images, and an overall lowest minimum bore diameter (OLMBD) of the minimum bore diameters is identified. A value other than the OLMBD is determined to be an effective minimum bore diameter of the container mouth.

28 Claims, 6 Drawing Sheets

(56) References Cited

U.S. PATENT DOCUMENTS

| | | | |
|---|---|---|---|
| 5,466,927 A * | 11/1995 | Kohler et al. | 250/223 B |
| 6,175,107 B1 | 1/2001 | Juvinall | |
| 6,198,102 B1 * | 3/2001 | Shepherd | 250/340 |
| 7,028,857 B2 * | 4/2006 | Peronek | 215/40 |
| 7,238,930 B2 | 7/2007 | Watanabe | |
| 7,436,509 B2 | 10/2008 | Diehr | |
| 2006/0140470 A1 | 6/2006 | Watanabe | |
| 2010/0225908 A1 * | 9/2010 | Kwirandt | 356/239.4 |
| 2011/0102782 A1 | 5/2011 | Wiemer et al. | |
| 2011/0102783 A1 | 5/2011 | Wiemer et al. | |
| 2013/0002851 A1 * | 1/2013 | Hall et al. | 348/92 |

* cited by examiner

CONTAINER INSPECTION APPARATUS AND METHOD

The present disclosure relates generally to inspection of containers and more particularly to an apparatus and method for detecting commercial variations in a container.

BACKGROUND AND SUMMARY OF THE DISCLOSURE

In the manufacture of containers, various anomalies can occur that affect the commercial acceptability of the containers. Such anomalies are known as "commercial variations" and can involve one or more attributes of the container. For example, commercial variations can include dimensional characteristics of the container at an open mouth of the container. Thus, it is often times useful to provide inspection equipment capable of inspecting the containers for commercial variations. The term "inspection" is used in its broadest sense to encompass any optical, electro-optical, mechanical or electrical observation or engagement with a container to measure or determine a container characteristic, including but not necessarily limited to commercial variations. U.S. patents that illustrate inspection processes of this type for glass containers include U.S. Pat. Nos. 5,461,228 and 6,175,107.

A general object of the present disclosure, in accordance with one aspect of the disclosure, is to provide a more reliable optical plug gage (OPG) apparatus and method for more accurately gaging a size of a container mouth bore.

The present disclosure embodies a number of aspects that can be implemented separately from or in combination with each other.

In accordance with an aspect of the disclosure, there is provided a method of inspecting a container having a base and a mouth. Light is directed through the container base into the container, and out of the container through the container mouth, using at least one light source disposed beneath the container base. A plurality of images of the container mouth is obtained from the light directed through the container mouth, and minimum bore diameters of the container mouth are calculated from the plurality of images. An overall lowest minimum bore diameter (OLMBD) of the minimum bore diameters is identified, and an effective minimum bore diameter of the container mouth is determined to be a value other than the OLMBD.

In accordance with another aspect of the disclosure, there is provided an apparatus for inspecting a container having a base and a mouth. At least one light source is disposed beneath the container base, wherein the light source directs light through the container base into the container, and out of the container through the container mouth. A light sensor is disposed with respect to the light source and the container to sense light transmitted through the container mouth. A processor acquires a plurality of images of the container mouth from the light sensor, calculates minimum bore diameters of the container mouth from the plurality of images, identifies an overall lowest minimum bore diameter (OLMBD) of the minimum bore diameters, and determines an effective minimum bore diameter of the container mouth to be a value other than the OLMBD.

BRIEF DESCRIPTION OF THE DRAWINGS

The disclosure, together with additional objects, features, advantages and aspects thereof, will be best understood from the following description, the appended claims and the accompanying drawings, in which:

DETAILED DESCRIPTION OF PREFERRED EMBODIMENTS

The present disclosure relates to a method of and apparatus for inspecting a container having a base and a mouth. It has been discovered that inspection of a bore diameter of a container mouth may be difficult because of various restrictions within the bore. For example, the restriction may be because of bore angle variations, perhaps due to "bent" container necks relative to the optics of the inspection apparatus, or occlusions low in the bore. It was also discovered that bore diameter measurement can be improved to account for such restrictions by determining an effective minimum bore diameter (EMBD) of a container mouth. Examples of related methods and apparatuses are described below.

Figures 1, 2:
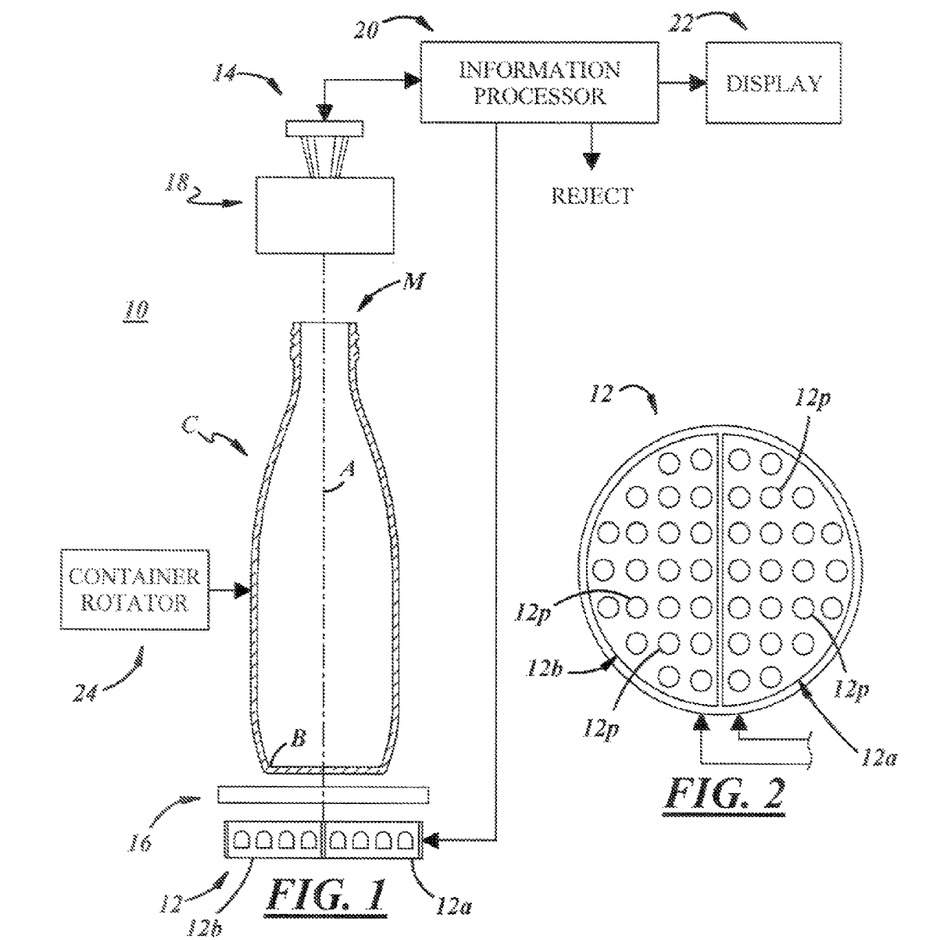
FIG. 1 is a schematic diagram of an optical plug gage apparatus for evaluating a mouth of a container in accordance with an exemplary embodiment of the present disclosure, and including first and second light sources.
FIG. 2 is a schematic top view of the light sources of FIG. 1.

FIG. 1 illustrates an exemplary embodiment of an inspection apparatus 10 for inspecting an open mouth M of a container C. The apparatus 10 may include an optical plug gage that may include one or more light sources 12 operatively disposed below the container C to produce light used in inspecting the container mouth M, and one or more light sensors 14 disposed above the container C to sense light produced by the light source 12 and passing through the container mouth M. As used herein, the terminology "operatively disposed" includes light sources that may be located anywhere but emit light from below the container C, for example, via mirrors, fiber optics or the like. The apparatus 10 optionally may include one or more light diffusers 16 disposed between the light source 12 and the container C to diffuse and/or direct light through a bottom B of the container C into the container C and through the container mouth M. The apparatus 10 further may include a lens system 18 disposed between the container C and the light sensor 14 to direct light passing through the container mouth M to the light sensor 14. The apparatus 10 additionally may include a processor 20 or any other suitable device(s) to scan the light sensor 14 and develop an image of the container mouth M and/or any other suitable inspection information, and a display 22 to display the image and/or other inspection information. The apparatus 10 also may include a container rotator 24 to rotate the container C.

The container C may be a jar, or a bottle as illustrated in FIG. 1, or any other suitable type of container. The container C may be composed of plastic, glass, or any other suitable material. The container C may be clear, colored, transparent, translucent, or of any other suitable optical quality.

Referring to FIGS. 1 and 2, the light source 12 may include any suitable device, article, or instrumentality to illuminate the container C. For example, the light source 12 may include a plurality of light sources 12a, 12b, each of which may include one or more discrete light elements 12p (FIG. 2). For example, the light source 12 may include at least two light sources 12a, 12b that may be diametrically opposed to one another and/or operatively disposed adjacent to each other beneath the container base B (FIG. 1), and that may be energized independently and alternatingly. The light sources 12a, 12b may be of any suitable circumferentially angular size. For example, one or both of the light sources 12a, 12b may have a circumferentially angular size of 180 degrees as illustrated in FIG. 2. In a further example, one or both of the light sources 12a, 12b may have a circumferentially angular size of 60 to 70 degrees and, more particularly, 65 degrees. In another example, the light elements 12p (FIG. 2) may include a plurality of light emitting diodes (LEDs), wherein the light source 12 may be a multiple-LED light source. In any case, those of ordinary skill in the art will recognize that the light source 12 may receive power from any suitable source in any suitable manner and may be controlled by the processor 20 (FIG. 1) in any suitable manner. Moreover, those of ordinary skill in the art will recognize that the light source 12 may be divided into sub-sections or sub-portions or may be composed of two separate light sources.

The plurality of light sources 12a, 12b may have differing operating characteristics. In one example embodiment, the light sources 12a, 12b may be energized alternatingly or sequentially, for example, with no overlap in emission of light. In another example embodiment, the light sources 12a, 12b may emit light of different wavelengths with simultaneous emission of light. Example different operating characteristics are disclosed in U.S. patent application Ser. No. 13/172,258, which is assigned to the assignee hereof and is incorporated by reference herein.

With reference to FIG. 1, the light sensor 14 may include any suitable device to sense or capture light or images. For example, the light sensor 14 may include an image sensor, for instance, a charge-coupled device (CCD), complementary metal-oxide-semiconductor (CMOS) device, or any other suitable image sensor. In another example, the light sensor 14 may include a photodiode device, a photoresistor device, or any other suitable photodetector device.

The light diffuser 16 may include any suitable device to diffuse light. For example, the light diffuser 16 may include a ground glass diffuser, a teflon diffuser, a holographic diffuser, an opal glass diffuser, a greyed glass diffuser, or any other suitable diffuser.

The lens system 18 may include any suitable device to direct or focus light. For example, the lens system 18 may include a telecentric lens, an entrance pupil, and pupil lenses on either side of the pupil. The lens system 18 may direct only light rays that emerge from the container mouth M essentially parallel to an axis A of the container C.

The processor 20 may include any suitable device(s) to read or acquire data or images from the light sensor 14, process the data or images, and output images to the display 22. In one example, the processor 20 may include the light sensor 14 itself. In another example, the processor 20 may be a device separate from the light sensor 14. In a further example, the processor 20 may include both of the aforementioned examples.

The container rotator 24 may include any suitable device to rotate the container C. For example, the rotator 24 may include one or more rollers, wheels, belts, discs, and/or any other suitable element(s) to rotate the container C. In another embodiment, the container C may remain stationary, and one or more of the various apparatus elements 12, 14, 16, 18 may be rotated in any suitable manner.

Figures 3A, 3B, 3C, 3E, 3F, 3G:
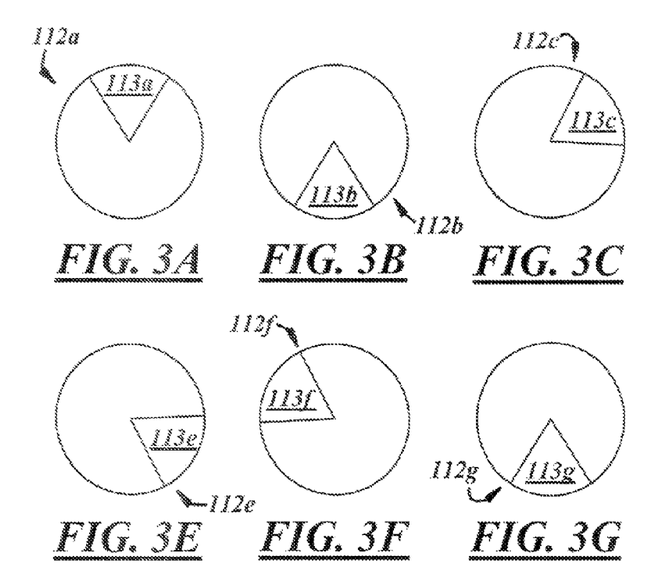
FIGS. 3A-3L are schematic views of light images produced by light captured by a light sensor and emanating from the light sources of FIG. 1 through the container mouth of FIG. 1.
Figure 3D:
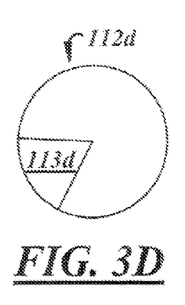
Figure 3H:
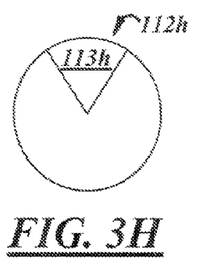
Figure 3I:
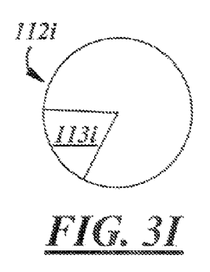
Figure 3J:
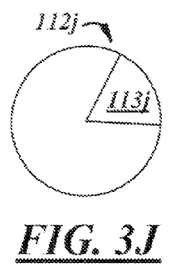
Figure 3K:
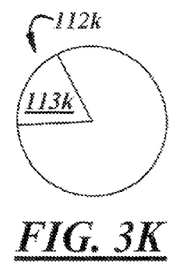
Figure 3L:
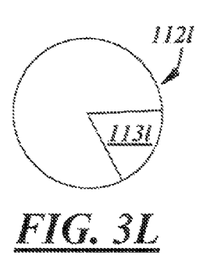

In one example of operation, the first light source 12a is energized, and light from that first light source 12a extending parallel to the container axis A and through the container mouth M is sensed by the light sensor 14 and a corresponding first image 112a may be acquired from the light sensor 14 by the processor 20 as shown in FIG. 3A. Any reflections that may impinge on one half of the sensor 14 may be digitally discarded, for example, by the information processor 20. Then, the first light source 12a is de-energized and the second light source 12b is energized and light from that second light source 12b extending parallel to the container axis A and through the container mouth M is sensed by the light sensor 14 and a corresponding second image 112b may be acquired from the light sensor 14 by the processor 20 as shown in FIG. 3B. Any reflections that may impinge on another half of the sensor 14 may be digitally discarded, for example, by the information processor 20.

Images of the container mouth M may be obtained in pairs, equally circumferentially spaced about the container mouth M. For example, the first image 112a (or light corresponding to the first image 112a) of the pair may be captured by the light sensor 14, and transfer of the image 112a from the light sensor 14 to the processor 20 is begun, then a short time (e.g. sub-millisecond) elapses, and thereafter the second image 112b of the pair is captured and transferred while the first image 112a is still being transferred to or acquired by the processor 20. Accordingly, the images 112a, 112b may be obtained selectively, sequentially, and synchronously.

In one embodiment, each of the images 112a, 112b may include approximately 180 circumferentially angular degrees of the container mouth M, but only select portions, for example, segment images 113a, 113b of the images 112a, 112b, may be further processed. For example, the processor 20 may apply any suitable digital masking or subtraction techniques to ignore image signals that do not correspond to the desired segment images 113a, 113b. The segment images 113a, 113b may be of corresponding segments of the container mouth M that may be of circumferentially angular size of 60 to 70 degrees and, more particularly, about 65 degrees. The segment images 113a, 113b can be assumed to be essentially free of low-angle reflections that would interfere with image processing. This is because regions of the container mouth M that are coincident with the divider of the light source 12 (or edges of the light sources 12a, 12b) could have some low-angle reflections. Accordingly, in this embodiment, only the segment images 113a, 113b of the images 112a, 112b may be evaluated. As used herein, the term "segment" includes a portion of an image, for example, cut off by one or more lines, for instance, an area of a circle bounded by one or more chords and an arc of that circle.

In other embodiments, the images 112a, 112b and the segment images 113a, 113b may be one and the same. For example, two opposed light sources smaller in circumferential angle than the light sources 12a, 12b may be used and may correspond to portions or segments of the container base B. In another example, a plurality of pairs of light sources smaller in circumferential angle than the light sources 12a, 12b may be used, wherein each pair of which may include two diametrically opposed light sources that correspond to portions or segments of the container base B. The aforementioned examples are disclosed in U.S. patent application Ser. No. 13/172,258, which is assigned to the assignee hereof and is incorporated by reference herein.

Any suitable circumferentially angular range of the segment images 113a, 113b may be used. For example, as shown in FIGS. 3A and 3B, an inspection angle of 65 circumferentially angular degrees may be used. Stated another way, an example circumferentially angular size of the segment images 113a, 113b may be about 36% of the circumferentially angular extent of the corresponding images 112a, 112b. Therefore, it may be desirable to obtain similar, additional, angularly adjacent image portions. This may be accomplished by rotating the container C and obtaining other pairs of segment images 113c through 133l of the container mouth M in the manner described above, and as shown in FIGS. 3C through 3L. The segment images 113a through 113l may circumferentially overlap one another.

Figure 4:
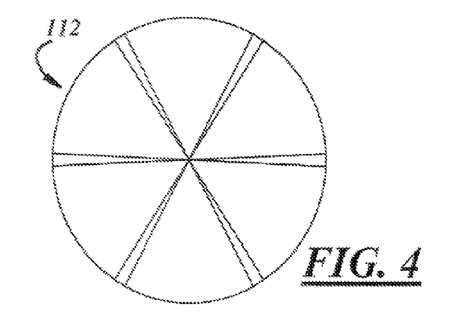
FIG. 4 is a schematic view of a composite light image produced from the light images of FIGS. 3A-3L.

As shown in FIG. 4, the images 112a through 112l and/or segment images 113a through 113l of FIGS. 3A-3L can be superimposed or added to obtain a complete image 112 of a bore or inside diameter of the container mouth M. The image 112 can be used to identify commercial variations in the container, measure the bore or inside diameter of the container mouth M, or for any other suitable container inspection techniques. Accordingly, the composite image 112 may be composed of the pairs of segment images 113a through 113l and may include a full 360 circumferentially angular degrees of the container mouth M. This may be particularly desirable for inspection of commercial variations or where a circumferentially continuous diametric measurement of the bore of the container mouth M. Those of ordinary skill in the art will recognize that more or less image portions or segment images may be obtained and evaluated, for example, twelve 35 to 40 degree segments, ten 40 to 45 degree segments, eight 50 to 55 degree segments, four 100 to 105 degree segments, and/or the like.

In an example illustrated by FIGS. 3A through 3L, the inspection angle may be set to 65 degrees in circumferential angular size and, thus, 130 degrees in circumferential angle of the container mouth M may be evaluated per each image frame (opposed pair of segment images). The container C may be rotated to move portions of the container mouth M through the inspection angle to obtain multiple image frames, preferably with some overlap between successive image frames.

Assuming the image frames are obtained and processed quickly enough that successive image frames provide for contiguous segment images, and because opposed segments of the container mouth M are being evaluated in each frame, 100% (or 360 degrees) of the container mouth can be inspected by rotating the container C only about one-half revolution (180 degrees) and obtaining a total of three frames (three opposed pairs of segment images). Accordingly, in this example, only three frames (FIGS. 3A-3F) may be used to establish a bore diameter for the container mouth M.

However, for more accurate measurement, the container C may be rotated for about one full revolution (360 degrees) and double the required number of frames, for example a total of six frames (six opposed pairs of segment images), may be captured by the sensor 14 and acquired and further processed by the processor 20. The first frame may include a first pair of opposed segment images 113a, 113b of images 112a, 112b, the second frame may include a second pair of opposed segment images 113c, 113d of images 112c, 112d circumferentially spaced from the first pair, and so on. In an example illustrated also by FIGS. 3E through 3L, additional pairs of segment images 113e, 113f; 113g, 113h; 113i, 113j; 113k, 113l may be obtained, for example, from images 112e, 112f; 112g, 112h; 112i, 112j; 112k, 112l. As shown in FIG. 4, the images 112a through 112l and/or segment images 113a through 113l may be superimposed or added to obtain a complete image 112 of the bore of the container mouth M.

According to a method of the present disclosure, the container C may be inspected to accurately calculate a bore diameter of the container mouth M.

As is known to those of ordinary skill in the art of container inspection, a reject diameter may be set for the bore of the container mouth. A nonlimiting example of the reject diameter may be any diameter less than 0.704 inches.

A plurality of images of the container mouth M may be obtained. For example, a plurality of images of segments of the container mouth M may be obtained. In one embodiment, light may be directed out of the container C through the container mouth M using, for instance, the light source 12, and that light may be sensed or captured by the light sensor 14, and images may be acquired from the light sensor 14 by the processor 20. In other embodiments, the plurality of images may be obtained in any other suitable manner, using any other suitable apparatus. The plurality of images of segments of the container mouth M may include a plurality of pairs of images of diametrically opposed segments of the container mouth M. For example, the plurality of images may include six pairs of images of corresponding diametrically opposed segments of the container mouth M.

According to the method, a minimum diameter of the bore of the container mouth M may be calculated for each frame of the segment images 113a through 113l, using any suitable image processing software. The segment images 113a through 113l correspond to the imaged diametrically opposed segments of the container mouth M. A first frame may include segment images 113a, 113b, a second frame may include segment images 113c, 113d, a third frame may include segment images 113e, 113f, a fourth frame may include segment images 113g, 113h, a fifth frame may include segment images 113i, 113j, and a sixth frame may include segment images 113k, 113l.

For instance, for the six frames, (1) through (6), the following example bore diameter values may be calculated (in inches):

(1) 0.710
(2) 0.702
(3) 0.708
(4) 0.712
(5) 0.706
(6) 0.711.

From the bore diameter values of the frames, an overall lowest minimum bore diameter (OLMBD) may be identified. For example, frame (2) may be identified as the OLMBD because it is lower than the other frames.

Also, groups of the frames may be evaluated to identify a group lowest minimum bore diameter (GLMBD) for each group. As used herein, the term "group" includes more than one but less than all of the frames. As an example, unique groups of frames and their GLMBD values may be as follows:

(1) frames 1, 2, and 3 (GLMBD=0.702)
(2) frames 2, 3, and 4 (GLMBD=0.702)
(3) frames 3, 4, and 5 (GLMBD=0.706)
(4) frames 4, 5, and 6 (GLMBD=0.706)
(5) frames 5, 6, and 1 (GLMBD=0.706)
(6) frames 6, 1, and 2 (GLMBD=0.702).

Each of the groups of the plurality of images may represent or cover at least 360 degrees of the circumference of the bore of the container mouth. Because each of the groups represents a sufficient amount of data to establish a bore diameter, variation in the GLMBD from group to group is an indication that the view through the bore is more restricted in groupings that have a lower GLMBD. The restriction may be because of bore angle variations (perhaps due to "bent" container necks) relative to the optics of the inspection apparatus, or occlusions low in the bore. Accordingly, the OLMBD may not provide a sufficiently accurate representation of the actual minimum bore diameter of the container mouth M.

Therefore, to account for such variations, bore diameter measurement can be improved by determining a value other than the OLMBD to be an effective minimum bore diameter (EMBD) of the container mouth M. In one embodiment, the highest GLMBD value of the groups may be identified as the EMBD of the container mouth M. For instance, 0.706 inches is the highest LMBD value of groups 1 through 6 and, therefore, is determined to be the EMBD of the container mouth M. In another embodiment, EMBD may be determined based on one or more of the calculated minimum bore diameters of the frames. For example, the EMBD may be determined to be any of the calculated minimum bore diameters of the frames that is greater than the OLMBD.

In an additional embodiment, the EMBD may be determined mathematically or statistically from the calculated minimum bore diameters of the frames. For instance, any suitable average of two or more of the calculated minimum bore diameters can be determined to be the EMBD. More specifically, a mean, median, or mode of two or more of the calculated minimum bore diameters can be determined to be the EMBD.

In a further embodiment, the EMBD may be determined mathematically or statistically from the group lowest minimum bore diameters (GLMBDs). For example, any suitable average of the calculated minimum bore diameters can be determined to be the EMBD, for instance, a mean, median, or mode.

According to the presently disclosed method, in a first half of container revolution frames (1) through (3) are evaluated and, in a second half of container revolution, frames (4) through (6) are evaluated. During the second half, portions of the bore of the container mouth M corresponding to frames (1) through (3) are situated 180 degrees from portions of the bore of the container mouth M corresponding to frames (4) through (6).

Because of production variations, any given portion of a bore of any given container is rarely perfectly aligned to the lens system 18 of the inspection apparatus 10. For example, if the container C had been rotated only one half revolution and only frames (1) through (3) had been obtained, the container C would have been rejected because the lowest minimum bore diameter, 0.702 inches from frame (2), would be below the reject threshold (0.704).

But the container C is preferably rotated for a full revolution and frames (1) through (6) preferably are obtained and processed as described above. The minimum bore diameter of 0.706 inches from frame (5) is assumed to be a more ideal view through the bore. Therefore, evaluation of double the minimum required segments of the bore may increase chances for a better alignment of the bore with the lens system 18 of the inspection apparatus 10, and may reduce the effect of occlusions in a low portion of the bore that is not of concern.

FIGS. 5 through 8 illustrate another illustrative embodiment of an inspection apparatus 110. This embodiment is similar in many respects to the embodiment of FIGS. 1 through 4 and like numerals between the embodiments generally designate like or corresponding elements throughout the several views of the drawing figures. Accordingly, the descriptions of the embodiments are incorporated into one another. Additionally, the description of the common subject matter generally may not be repeated here.

Figures 5, 6:
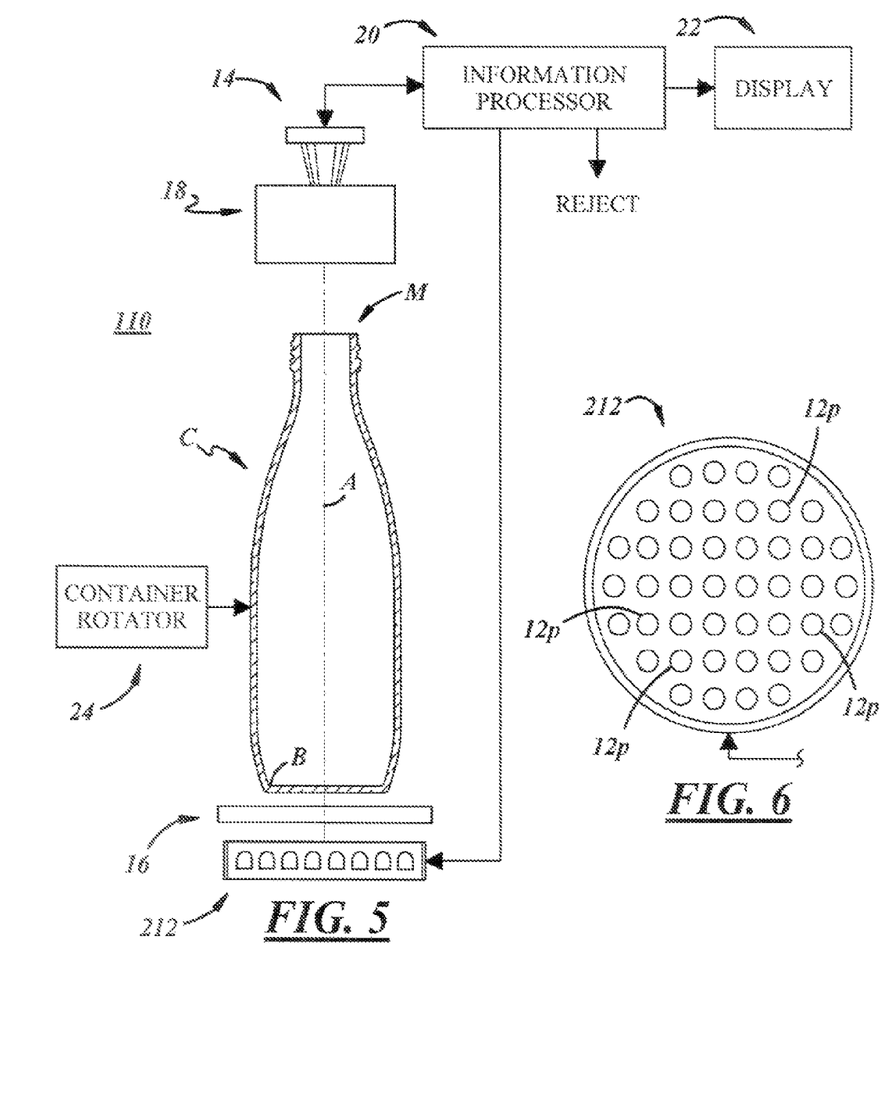
FIG. 5 is a schematic diagram of an optical plug gage apparatus for evaluating a mouth of a container in accordance with another exemplary embodiment of the present disclosure, and including a single light source.
FIG. 6 is a schematic top view of the light source of FIG. 5.

The apparatus 110 may include an optical plug gage that may include a light source 212 operatively disposed below the container C to produce light used in inspecting the container mouth M.

Referring to FIGS. 5 and 6, the light source 212 may include a single source of light and may include any suitable device, article, or instrumentality to illuminate the container C. For example, the light source 212 may include one or more discrete light elements 12$p$ (FIG. 6). The light source 212 may be of any suitable circumferentially angular size, for example, 360 degrees as illustrated in FIG. 6.

Figure 7A:
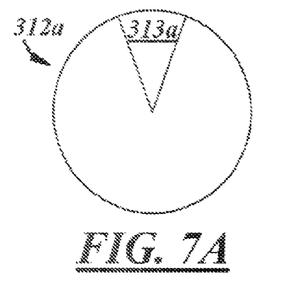
FIGS. 7A-7X are schematic views of light images produced by light captured by a light sensor and emanating from the light source of FIG. 5 through the container mouth of FIG. 5.
Figure 7B:
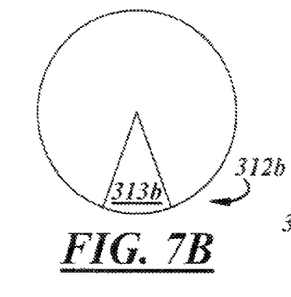

In one example of operation, the light source 212 is energized, and light from the light source 212 extending parallel to the container axis A and through the container mouth M is sensed by the light sensor 14 and corresponding first and second images 312$a$, 312$b$ may be acquired from the light sensor 14 by the processor 20 as shown in FIGS. 7A and 7B.

Images of the container mouth M may be obtained in pairs, equally circumferentially spaced about the container mouth M. In one embodiment, only select portions of the images 312$a$, 312$b$, for example, segment images 313$a$, 313$b$ may be further processed. For example, the processor 20 may apply any suitable digital masking or subtraction techniques to ignore image signals that do not correspond to the desired segment images 313$a$, 313$b$.

Figure 7C:
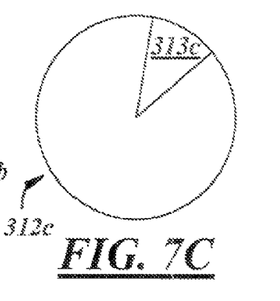
Figures 7D, 7E:
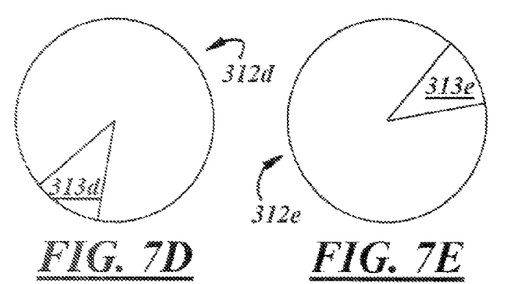
Figure 7F:
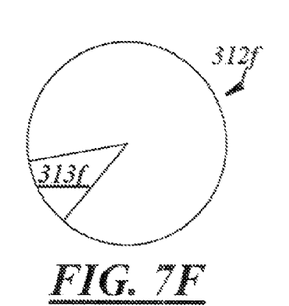
Figure 7G:
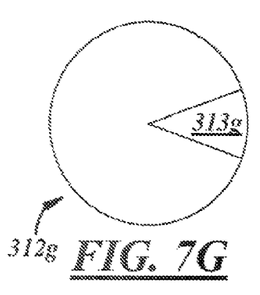
Figure 7H:
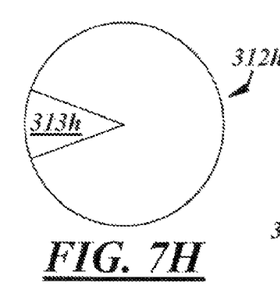
Figure 7I:
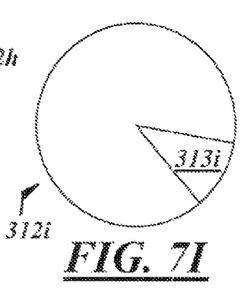
Figure 7J:
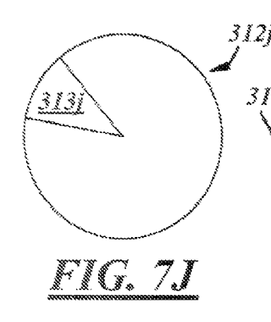
Figure 7K:
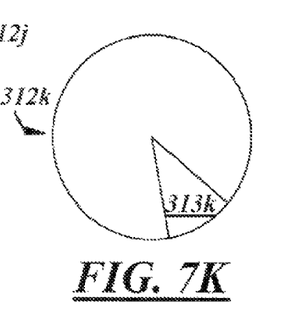
Figure 7L:
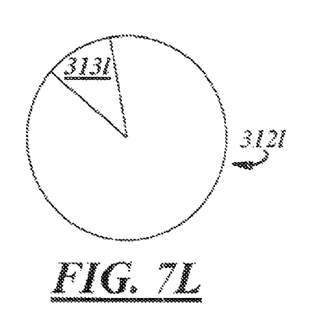
Figure 7M:
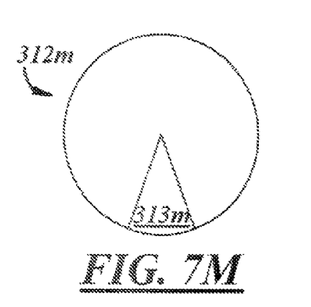
Figure 7N:
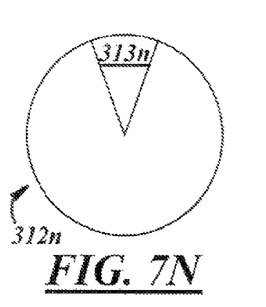
Figure 7O:
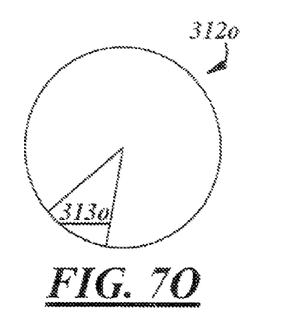
Figure 7P:
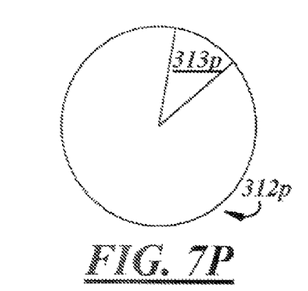
Figure 7Q:
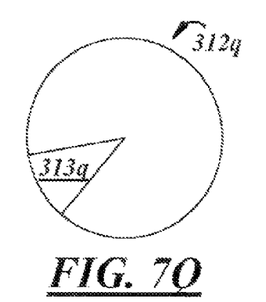
Figure 7R:
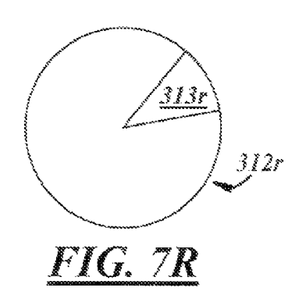
Figure 7S:
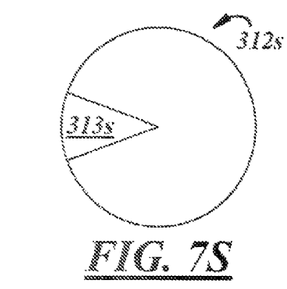
Figure 7T:
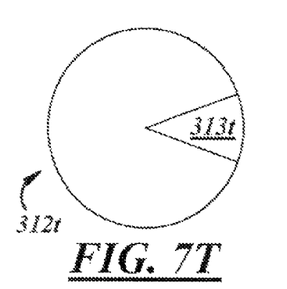
Figure 7U:
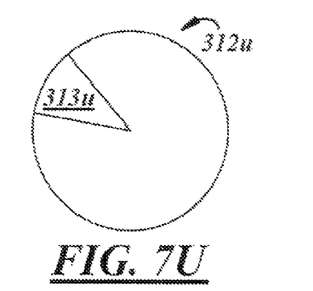
Figure 7V:
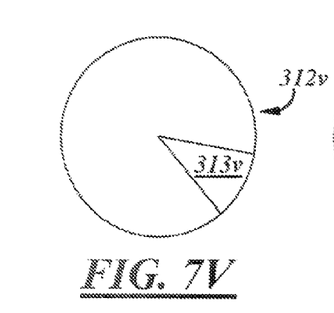
Figure 7W:
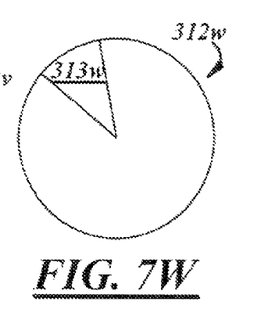

The segment images 313$a$, 313$b$ may be of corresponding segments of the container mouth M that may be of about 40 degrees in circumferentially angular size, for example, 35 to 45 degrees, or any other suitable circumferentially angular size. Stated another way, an example circumferentially angular size of the segment images 313$a$, 313$b$ may be about 22% of the circumferentially angular extent of the corresponding images 312$a$, 312$b$. The container C may be rotated to obtain additional pairs of segment images 313$c$ through 313$x$ of the container mouth M in the manner described above, and as shown in FIGS. 7C through 7X. The segment images 313$a$ through 313$x$ may circumferentially overlap one another.

Figure 8:
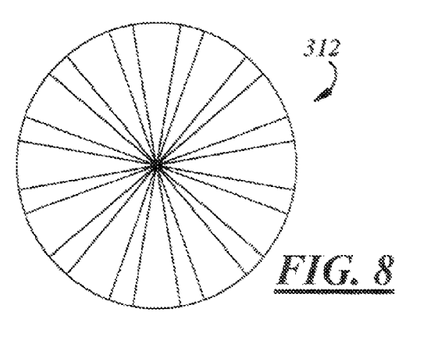
FIG. 8 is a schematic view of a composite light image produced from the light images of FIGS. 7A-7X.

As shown in FIG. 8, the images 312$a$ through 312$x$ and/or segment images 313$a$ through 313$x$ can be superimposed or added to obtain a complete image 312 of a bore or inside diameter of the container mouth M. The image 312 can be used to identify commercial variations in the container C, measure the bore or inside diameter of the container mouth M, or for any other suitable container inspection techniques. Accordingly, the composite image 312 may be composed of the pairs of segment images 313$a$ through 313$x$ and may include a full 360 circumferentially angular degrees of the container mouth M.

Figure 7X:
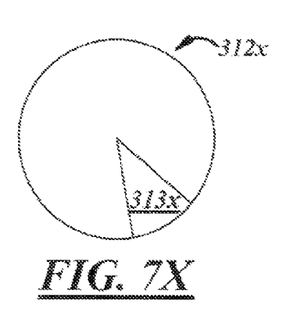

In an example illustrated by FIGS. 7A through 7X, the inspection angle may be set to 40 degrees in circumferential angular size and, thus, 80 degrees in circumferential angle of the container mouth M may be evaluated per each image frame (opposed pair of segment images). The container C may be rotated to move portions of the container mouth M through the inspection angle to obtain multiple image frames, preferably with some overlap between successive image frames.

Assuming the image frames are obtained and processed quickly enough that successive image frames provide for contiguous segment images, and because opposed segments of the container mouth M are being evaluated in each frame, 100% (or 360 degrees) of the container mouth M can be inspected by rotating the container C only about one-half revolution (180 degrees) and obtaining a total of six frames (six opposed pairs of segment images). Accordingly, in this example, only six frames (FIGS. 7A-7L) may be used to establish a bore diameter for the container mouth M.

For more accurate measurement, however, the container C may be rotated for about one full revolution (360 degrees) and double the required number of frames, for example a total of twelve frames (twelve opposed pairs of segment images), may be captured by the sensor 14 and acquired and further processed by the processor 20. The first frame may include a first pair of opposed segment images 313a, 313b of images 312a, 312b, the second frame may include a second pair of opposed segment images 313c, 313d of images 312c, 312d circumferentially spaced from the first pair, and so on. In an example illustrated also by FIGS. 7E through 7X, additional pairs of segment images 313e, 313f; 313g, 313h; 313i, 313j; 313k, 313l; 313m, 313n; 313o, 313p; 313q, 313r; 313s, 313t; 313u, 313v; 313w, 313x may be obtained, for example, from images 312e through 312x. As shown in FIG. 8, the images 312a through 312x and/or segment images 313a through 313x may be superimposed or added to obtain a complete image 312 of the bore of the container mouth M.

The minimum diameter of the bore of the container mouth M may be calculated for each frame of the segment images 313a through 313x, using any suitable image processing software. The segment images 313a through 313x correspond to the imaged diametrically opposed segments of the container mouth M. A first frame may include segment images 313a, 313b, a second frame may include segment images 313c, 313d, and so on. Bore diameter values may be calculated for each of twelve frames, as per the discussion above with respect to the embodiment of FIGS. 1 through 4. Likewise, unique groups of the twelve frames may be evaluated to identify a group lowest minimum bore diameter (GLMBD) for each group.

Similarly, as discussed with respect to the embodiment of FIGS. 1 through 4, bore diameter measurement can be improved by determining a value other than the OLMBD to be an effective minimum bore diameter (EMBD) of the container mouth M. This determination may include, but is not limited to determining the highest GLMBD value of the groups to be the EMBD of the container mouth M.

FIGS. 9A through 9D show an illustrative embodiment of light images that may be produced by light captured by the light sensor 14 and emanating from the light source 212 of FIG. 5 through the container mouth M of FIG. 5. This embodiment is similar in many respects to the embodiments of FIGS. 1 through 8 and like numerals between the embodiments generally designate like or corresponding elements throughout the several views of the drawing figures. Accordingly, the descriptions of the embodiments are incorporated into one another. Additionally, the description of the common subject matter generally may not be repeated here.

Figure 9A:
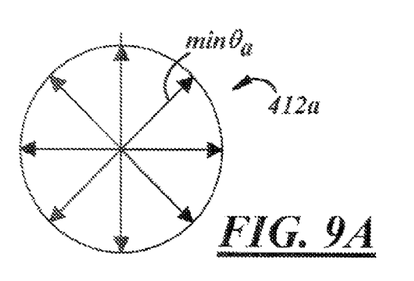
FIG. 9A is a schematic view of a light image produced by light captured by a light sensor and emanating from the light source of FIG. 5 through the container mouth of FIG. 5, with the container in a first position.
Figure 9B:
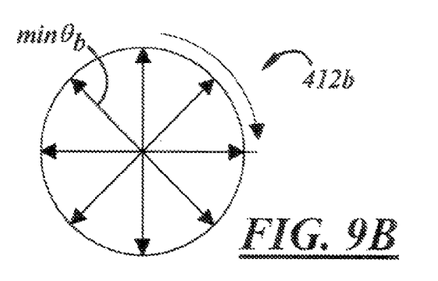
FIG. 9B is a schematic view of a light image similar to FIG. 9A, but with the container in a second position rotated with respect to the first position.
Figure 9C:
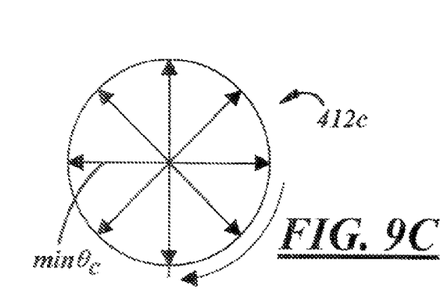
FIG. 9C is a schematic view of a light image similar to FIG. 9B, but with the container in a third position rotated with respect to the second position.
Figure 9D:
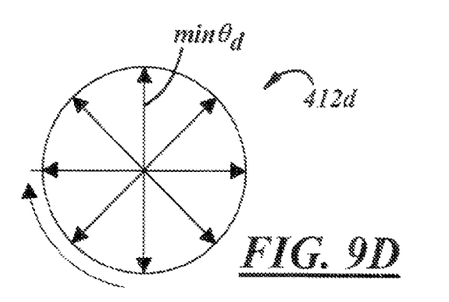
FIG. 9D is a schematic view of a light image similar to FIG. 9C, but with the container in a fourth position rotated with respect to the third position.

A plurality of images of the container mouth M may be obtained. For example, the obtained plurality of images each may represent or cover the entire circumference of the bore of the container mouth. In one embodiment, the light source 212 may be energized, and light from that light source 212 extending parallel to the container axis A and through the container mouth M may be sensed by the light sensor 14, and a first image 412a may be acquired from the light sensor 14 by the processor 20 as shown in FIG. 9A. Then, the container C may be rotated, for example, ninety degrees about its axis A. Thereafter, the light source 212 may be energized, and light from that light source 212 extending parallel to the container axis A and through the container mouth M may be sensed by the light sensor 14, and a second image 412b may be acquired from the light sensor 14 by the processor 20 as shown in FIG. 9B. Then, the container C may be rotated again, for example, ninety degrees about its axis A, and a third image 412c may be acquired as shown in FIG. 9C. Then, the container C may be rotated again, for example, ninety degrees about its axis A, and a fourth image 412d may be acquired as shown in FIG. 9D.

In the example above, the container mouth M may be imaged four times in increments of ninety degree rotation about its axis A. But any suitable plurality of images of the container mouth M may be obtained in the aforementioned manner, for example, two or more, and in any suitable increments of angular rotation about the container axis A. It is contemplated, however, that the quantity of images and rotational increments may be application specific and may depend on the speed of the inspection equipment and the maximum cycle time allotted for the inspection process.

In any case, any suitable quantity of minimum bore diameters (e.g. $\min\theta_a$, $\min\theta_b$, $\min\theta_c$, $\min\theta_d$) of the container mouth M may be calculated for the images 412a through 412d. The calculation may include taking a plurality of measurements of the bore diameter of the container mouth M for each of the obtained plurality of images. For example, 3,600 individual measurements of the bore diameter may be taken. Then, the calculation may include identifying the smallest of the plurality of measurements of each of the plurality of images as the calculated minimum bore diameter for each of the plurality of images. For instance, for the four images 412a through 412d, the following example minimum bore diameter values may be calculated (in inches):

(1) 0.702
(2) 0.708
(3) 0.712
(4) 0.706.

From the bore diameter values of the images, an overall lowest minimum bore diameter (OLMBD) may be identified. For example, frame (1) may be identified to be the OLMBD because it is lower than the other frames. Again, the OLMBD may not provide a sufficiently accurate representation of an actual minimum bore diameter of the container mouth M.

Therefore, bore diameter measurement can be improved by determining the EMBD of the container mouth M to be a value other than the OLMBD. For example, the EMBD may be determined based on one or more of the calculated minimum bore diameters (e.g. $\min\theta_a$, $\min\theta_b$, $\min\theta_c$, $\min\theta_d$). In one embodiment, the EMBD may be determined to be any of the calculated minimum bore diameters that is greater than the OLMBD. In another embodiment, the EMBD may be determined to be the highest of the calculated minimum bore diameters. For instance, 0.712 inches is the highest minimum value of the images 412a through 412d and, therefore, may be determined to be the EMBD of the container mouth M.

In an additional embodiment, the EMBD may be determined mathematically or statistically from the calculated minimum bore diameters. For instance, any suitable average of two or more of the calculated minimum bore diameters can be determined to be the EMBD. More specifically, a mean, median, or mode of two or more of the calculated minimum bore diameters can be determined to be the EMBD.

Accordingly, the presently disclosed methods may use oversampling of data to provide more accurate optical plug gage bore measurement to prevent false rejects. For instance, multiple segment images of the same or similar portions of the bore of the container mouth M may be obtained, wherein an obstructed reading may be ignored and an unobstructed reading may be preserved, to offset optical misalignment effects that may result from container production and handling variations.

There thus has been disclosed a container inspection apparatus and method, that satisfies one or more of the objects and aims previously set forth. The disclosure has been presented in conjunction with several illustrative embodiments, and additional modifications and variations have been discussed. Other modifications and variations readily will suggest themselves to persons of ordinary skill in the art in view of the foregoing discussion. The disclosure is intended to embrace all such modifications and variations as fall within the spirit and broad scope of the appended claims.

The invention claimed is:

1. A method of inspecting a container having a base and a mouth, including the steps of:
   directing light through the container base into the container, and out of the container through the container mouth, using at least one light source beneath the container base;
   obtaining a plurality of images of the container mouth from the light directed through the container mouth;
   calculating a plurality of minimum bore diameters of the container mouth from the plurality of images;
   identifying an overall lowest minimum bore diameter (OLMBD) of the plurality of minimum bore diameters; and
   determining an effective minimum bore diameter of the container mouth as being a value other than the OLMBD.

2. The method of claim 1 wherein each of the obtained plurality of images covers the entire circumference of the bore of the container mouth.

3. The method of claim 2 wherein the obtained plurality of images includes at least three images of the entire circumference of the bore of the container mouth.

4. The method of claim 2 wherein the obtained plurality of images includes at least four images of the entire circumference of the bore of the container mouth.

5. The method of claim 1 wherein the calculating step includes taking a plurality of measurements of the bore diameter of the container mouth for each of the obtained plurality of images and identifying the smallest of the plurality of measurements of each of the plurality of images as a calculated minimum bore diameter for each of the plurality of images.

6. The method of claim 1 wherein the determining step includes determining the effective minimum bore diameter of the container mouth based on at least one of the plurality of calculated minimum bore diameters.

7. The method of claim 6 wherein the determining step includes determining the effective minimum bore diameter of the container mouth as being one of the plurality of calculated minimum bore diameters other than the OLMBD.

8. The method of claim 7 wherein the determining step includes determining the effective minimum bore diameter of the container mouth as being the highest of the plurality of calculated minimum bore diameters other than the OLMBD.

9. The method of claim 6 wherein the obtained plurality of images includes a plurality of images of segments of the container mouth, wherein the identifying step includes evaluating groups of the plurality of images to identify a group lowest minimum bore diameter (GLMBD) for each of the groups, and the determining step includes determining the highest GLMBD as the effective minimum bore diameter of the container mouth.

10. The method of claim 9 wherein each of the groups of the plurality of images is different from every other of the groups of the plurality of images.

11. The method of claim 9 wherein each of the groups of the plurality of images covers at least 360 degrees of the circumference of the bore of the container mouth.

12. The method of claim 9 wherein the obtaining step includes obtaining the plurality of images as a plurality of pairs of images of diametrically opposed segments of the container mouth.

13. The method of claim 12 wherein the obtaining step also includes rotating the container to different circumferentially angular positions for obtaining the plurality of pairs of images of diametrically opposed segments of the container mouth.

14. The method of claim 12 wherein the plurality of pairs of images includes six pairs of images about 65 degrees in circumferentially angular size, and wherein a minimum diameter of the bore of the container mouth is calculated for each of the six pairs of images.

15. The method of claim 12 wherein the plurality of pairs of images includes twelve pairs of images about 40 degrees in circumferentially angular size, and wherein a minimum diameter of the bore of the container mouth is calculated for each of the twelve pairs of images.

16. The method of claim 12 wherein unique groups of the plurality of pairs of images are evaluated to calculate the GLMBD.

17. The method of claim 1 wherein the light source is a single light source.

18. The method of claim 1 wherein the light source includes at least first and second light sources operatively disposed adjacent to each other beneath the container base.

19. The method of claim 1 including diffusing the light directed into the container.

20. The method of claim 1 wherein the directing step includes focusing the light before the light is sensed.

21. An apparatus for inspecting a container having a base and a mouth, the apparatus including:
   at least one light source disposed beneath the container base, wherein the light source directs light through the container base into the container, and out of the container through the container mouth;
   a light sensor disposed with respect to the light source and the container to sense light transmitted through the container mouth; and
   a processor for acquiring a plurality of images of the container mouth from the light sensor, calculating a plurality of minimum bore diameters of the container mouth from the plurality of images, identifying an overall lowest minimum bore diameter (OLMBD) of the plurality of minimum bore diameters, and determining an effective minimum bore diameter of the container mouth as being a value other than the OLMBD.

22. The apparatus of claim 21 wherein the light source is a single light source.

23. The apparatus of claim 21 wherein the light source includes at least first and second light sources operatively disposed adjacent to each other beneath the container base.

24. The apparatus set forth in claim 21 wherein each of the light sources includes one or more discrete light elements.

25. The apparatus set forth in claim 21, including a light diffuser disposed between the light source and the container.

26. The apparatus set forth in claim 21, including a lens system disposed between the container and the light sensor.

27. The apparatus set forth in claim 21, wherein the light sensor captures the plurality of images in opposed pairs of images.

28. The apparatus set forth in claim 27, including a container rotator to rotate the container to different angular positions for capturing additional opposed pairs of images.

* * * * *